United States Patent [19]

Malz et al.

[11] Patent Number: 5,420,354

[45] Date of Patent: May 30, 1995

[54] PROCESS OF PREPARING PARA PHENYLAMINES

[75] Inventors: Russell E. Malz, Naugatuck, Conn.; Gerard V. Smith, Carbondale, Ill.; Mark P. Ferrandino, Danbury, Conn.; Ruozhi Song, Carbondale, Ill.

[73] Assignee: Uniroyal Chemical Company, Inc., Middlebury, Conn.

[21] Appl. No.: 318,928

[22] Filed: Oct. 6, 1994

[51] Int. Cl.$^6$ .............................................. C07C 209/36
[52] U.S. Cl. .................................. 564/423; 564/395; 564/420; 564/422; 564/434
[58] Field of Search ............... 564/395, 416, 420, 422, 564/423, 421, 433, 434, 435

[56] References Cited

U.S. PATENT DOCUMENTS

| | | | |
|---|---|---|---|
| 2,714,614 | 8/1955 | Weinmayr | 260/571 |
| 2,974,169 | 3/1961 | Newby | 206/576 |
| 3,285,972 | 11/1966 | Young | 260/621 |
| 3,715,397 | 2/1973 | Rylander | 260/575 |
| 3,748,362 | 7/1973 | Klastler | 260/576 |
| 3,953,509 | 4/1976 | Greco | 260/580 |
| 4,034,042 | 7/1977 | Wedemeyer | 260/576 |
| 4,155,936 | 5/1979 | Sturm | 260/576 |
| 4,313,002 | 1/1982 | Symon et al. | 564/423 |
| 4,518,803 | 5/1985 | Batorewicz | 564/410 |
| 5,068,439 | 11/1991 | Cottman | 564/434 |

OTHER PUBLICATIONS

H. E. Heller et al., *Nature*, 168 (1951) 909.

C. K. Ingold, *Structure and Mechanism of Organic Chemistry*, Cornell University Press, New York, 1953, pp. 622–623.

A. v. Baeyer et al., *Justus Liebig's Annalen Der Chemie*, 390, (1912), pp. 139–144. (with translation).

A. v. Baeyer et al., *Justus Liebig's Annalen Der Chemie*, 424, (1921), pp. 233, 243–245, 294–296. (with translation).

*Primary Examiner*—Peter O'Sullivan
*Attorney, Agent, or Firm*—Raymond D. Thompson

[57] ABSTRACT

A process of preparing para phenylenediamines, such as, p-aminodiphenylamine. The process involves contacting nitrobenzene or a substituted derivative thereof with hydrogen and an amine, such as aniline, in the presence of a hydrogenation catalyst, a hydrogenation inhibitor, and an acid cocatalyst under reaction conditions.

22 Claims, No Drawings

PROCESS OF PREPARING PARA PHENYLAMINES

BACKGROUND OF THE INVENTION

This invention relates to a process of preparing para phenylenediamines, such as p-aminodiphenylamine.

Para phenylenediamines find a variety of utilities depending upon the para substituent. As an example, p-aminodiphenylamine is an important intermediate in the synthesis of rubber antioxidants and antiozonants. Other p-phenylenediamines, particularly $C_{5-10}$ alkyl-substituted derivatives thereof, are also useful in stabilizing rubbers.

The syntheses of para phenylenediamines vary depending upon the para substituent and often require several steps which add undesirably to the production costs.

It would be advantageous to have a general, one-step process to produce para phenylenediamines. It would be more advantageous if the process did not produce significant quantities of undesirable by-products and intermediates, such as nitrosamines. It would be even more advantageous if the process did not use a liquid acid catalyst, since such a catalyst requires neutralization which leads to a waste salt stream. It would be most advantageous if the process employed a heterogeneous catalyst, so that the separation of the catalyst from the product stream is simple and inexpensive. With these multiple advantages, the process would be amenable to commercial application.

SUMMARY OF THE INVENTION

This invention is a process of preparing para phenylenediamines. The process comprises contacting nitrobenzene or a substituted derivative thereof with hydrogen and an amine. The amounts of hydrogen and amine relative to the nitrobenzene are sufficient to produce the desired para phenylenediamine product. The contacting is conducted in the presence of catalytic amounts of a hydrogenation catalyst in combination with a hydrogenation inhibitor and an acid cocatalyst under reaction conditions such that para phenylenediamine or a substituted derivative thereof is formed.

Advantageously, the process of this invention produces para phenylenediamines in one step by combining nitrobenzene or a substituted nitrobenzene with hydrogen and an amine. More advantageously, the process of this invention does not produce nitrosamines as intermediates. In certain embodiments to be described hereinbelow, the catalysts are heterogeneous, and are therefore simply and inexpensively separated from the product stream. No neutralization of liquid acid is required and there is no formation of a waste salt stream.

DETAILED DESCRIPTION OF THE INVENTION

In accordance with the process of this invention, nitrobenzene or a substituted nitrobenzene is contacted with hydrogen and an amine in the presence of catalytic amounts of an acid cocatalyst and a hydrogenation catalyst combined with a hydrogenation inhibitor to yield para phenylenediamine or a substituted derivative thereof. In a preferred embodiment of this invention, nitrobenzene is contacted with hydrogen and aniline in the presence of a hydrogenation catalyst, a hydrogenation inhibitor, and an acid cocatalyst to yield p-aminodiphenylamine.

Nitrobenzenes which are suitable for the process of this invention include nitrobenzene and substituted nitrobenzenes provided that the substituent(s) is(are) inert with respect to the process of this invention. In addition, the inert substituent(s) should be located at a position other than the para position relative to the nitro moiety. The para position should remain unsubstituted, because it is this position which is involved in the reaction with the amine. Suitable substituents include linear and branched $C_{1-10}$ alkyl moieties, as well as amino ($-NH_2$), hydroxyl, keto [$-C(O)R$], and ester moieties [$-OC(O)R$], wherein the R substituent is preferably a $C_{1-10}$ alkyl or a $C_{6-10}$ aryl or alkaryl group. Non-limiting examples of substituted nitrobenzenes include compounds such as nitrotoluene, nitroethylbenzene, nitrocumene, and nitrophenol. Preferably, the nitrobenzene is unsubstituted or is substituted with a $C_{1-10}$ alkyl moiety. More preferably, the nitrobenzene is unsubstituted.

Hydrogen is required for the process of this invention and may be supplied as pure gaseous hydrogen or as a mixture of hydrogen with an inert diluent. The term "inert" means that the diluent is non-reactive in the process of this invention. Suitable inert diluents include helium, nitrogen, and argon. If an inert diluent is employed, the concentration of hydrogen can range broadly from about 1 to about 99 volume percent of the hydrogen-diluent stream, as desired. The molar ratio of hydrogen to nitrobenzene or substituted nitrobenzene can be any ratio which yields the desired para phenylenediamine product. Typically, the molar ratio of hydrogen to the nitrobenzene varies from about 2 to about 50, preferably from about 2 to about 30. Below the lower preferred molar ratio there may not be sufficient hydrogen present for complete conversion of the nitrobenzene reactant.

An amine is also required for the process of this invention. Any amine is suitable provided that the amine is capable of combining with the nitrobenzene to form para phenylenediamine. Suitable amines include ammonia, aliphatic amines, alicyclic amines, aryl amines and alkaryl amines. Non-limiting examples of suitable aliphatic amines include primary and secondary, linear and branched $C_{1-20}$ alkyl amines, such as methylamine, dimethylamine, ethylamine, diethylamine, propylamine, dipropylamine, isopropylamine, diisopropylamine, butylamine, dibutylamine, and higher homologues and isomers of these compounds. Also suitable are mixed alkylamines, such as methylethylamine, ethylpropylamine and the like. Non-limiting examples of alicyclic amines include $C_{4-8}$ alicyclic amines, such as, cyclopentylamine and cyclohexylamine. Suitable examples of aryl and alkaryl amines include $C_{6-15}$ aryl or alkaryl amines, such as aniline, toluidine, dimethylaniline, ethylphenylamine, propylphenylamine, isopropylphenylamine, naphthylamine, and the like. The preferred amines are ammonia, $C_{1-10}$ alkylamines, and $C_{6-15}$ aryl and alkaryl amines. Even more preferred are aniline and $C_{1-5}$ alkyl-substituted anilines. The most preferred amine is aniline.

Any molar ratio of amine to the nitrobenzene is suitable for the process of this invention provided that a para phenylenediamine is obtained as a product. When the amine is a liquid under the process conditions, the amine may also act as a solvent for the process. Consequently, the amount of amine employed relative to the nitrobenzene is generally large. Suitable molar ratios of amine to the nitrobenzene are typically equal to or greater than 2. Preferably, this molar ratio ranges from 2 to about 25, more preferably, from 2 to about 10. Ratios below 2 may also be suitable.

If the amine is a solid, it may be desirable to conduct the process of this invention in the presence of an inert solvent. The term "inert" means that the solvent is non-reactive towards the reagents, products, and catalysts of the process, and therefore, does not interfere with the process of this invention. Any inert solvent is suitable so long as it provides the intended solubilization, and so long as a para phenylenediamine is obtained as a product. Suitable solvents include common hydrocarbons liquid at room temperature, such as toluene, as well as polar organic solvents, such as cyclohexanol. If desired, the amine selected for the process, such as aniline, may also be used as a solvent. If a solvent is employed, the quantity varies depending upon the solubilities of the specific reagents and products involved. One skilled in the art can readily determine an acceptable quantity of solvent. As a general rule, the ratio of moles of solvent to moles of the nitrobenzene is between about 2 and about 20, and is preferably between about 2 and about 10.

The hydrogenation catalyst which is employed is any which produces a para phenylenediamine in the process of this invention. Acceptable hydrogenation catalysts comprise the Group VIII metals of the Periodic Table, including iron, cobalt, nickel, rhodium, ruthenium, palladium, osmium, iridium and platinum. Molybdenum and copper are also suitable. Preferably, the hydrogenation catalyst is palladium or platinum, even more preferably, platinum. Generally, the hydrogenation catalyst is supported, for example, in an amount from about 0.05 to about 20 weight percent on a suitable support, such as carbon or alumina. The hydrogenation catalysts may be supported in their elemental form or supported as their oxides. If supported as the oxide, then the active elemental form of the catalyst is produced in situ under the process conditions of this invention.

The aforementioned hydrogenation catalysts are employed with a hydrogenation inhibitor. The inhibitor functions to stop the hydrogenation of the nitro moiety at the phenylhydroxylamine stage, as opposed to allowing the hydrogenation to proceed completely to the amine stage. Any compound capable of this inhibition is suitable, but preferred inhibitors include sulfur-containing organic compounds, such as dialkyl sulfoxides, preferably, dimethylsulfoxide (DMSO); alkyl sulfides, preferably, dimethyl sulfide; and mercaptans, preferably, 1-pentanethiol. Also acceptable as hydrogenation inhibitors are cyclic N-heterocycles, such as, pyrolidine and piperidine. The quantity of hydrogenation inhibitor typically ranges from about 0.01 mole to about 100 moles based on the weight of the platinum group metal.

Other suitable hydrogenation catalysts combine the hydrogenation metal and hydrogenation inhibitor in one compound. Examples of these include noble and base metal sulfides, such as, platinum sulfide and molybdenum sulfide, preferably supported on carbon. The preparation of these catalysts is described in U.S. Pat. No. 3,953,509, relevant sections of which are incorporated herein by reference.

The acid cocatalyst employed in the process of this invention is any homogeneous or heterogeneous acid catalyst capable of producing a para phenylenediamine in the process of this invention. Suitable homogeneous acid cocatalysts will dissolve in the liquid phase reaction mixture. Such cocatalysts include concentrated inorganic acids, such as hydrochloric, hydrobromic, and sulfuric acids, as well as organic acids, such as trifluoroacetic acid. The term "concentrated" is taken to mean a concentration, generally in an aqueous medium, of greater than about 6M. Preferably, the concentration is greater than about 8M, and more preferably, is between about 10M and about 12M.

Suitable heterogeneous solid acid cocatalysts include the metal oxides and mixed metal oxides of Groups IVA (Ti, Zr, Hf) and VA (V, Nb, Ta) of the Periodic Table, as well as, the oxides of aluminum and silicon. Non-limiting examples of this group include silica, alumina, silica-aluminas, titania, zirconia, and niobium oxide. Preferred among this group are silica-aluminas, silicas, and aluminum oxides.

Other suitable solid acid cocatalysts include acidic clays, such as montmorillonite and Filtrol™ brand acid clays. Also, suitable are acidic crystalline microporous aluminosilicate zeolites, including, zeolites X, Y, ZSM-5, and mordenite. Preferred among this group are zeolites Y and ZSM-5 in the acid form and Filtrol™ brand acid clay. Inasmuch as many zeolites are purchased or synthesized in the alkali or alkaline earth form, it may be necessary to convert the zeolite to its acid form. Techniques for doing this are well known to the skilled artisan. Typically, the metal ion form of the zeolite is stirred in an aqueous solution of an inorganic acid, such as hydrochloric or nitric acid, until all or a portion of the metal ion sites have been ion-exchanged for the acid form.

Other suitable solid acid cocatalysts include insoluble acidic cationic exchange resins, such as, poly(perfluoroalkylene)sulfonic acid, available as Nafion® brand; or macroporous sulfonated crosslinked polystyrenes or the corresponding styrene/acrylate copolymers available as Amberlite® brand. Preferred among this group is Nafion® poly(perfluoroalkylene) sulfonic acid.

The process of this invention may be conducted in any standard reactor, such as a stirred batch reactor; a fixed-bed, continuous flow reactor; a fluidized bed reactor; or a transport reactor. In a preferred design the hydrogenation catalyst and the acid cocatalyst are heterogeneous, so that the separation of the catalysts from the reaction stream presents no problem. The hydrogenation catalyst may even be supported on the solid acid cocatalyst. The process may be conducted, for example, in a batch reactor with the hydrogenation inhibitor being part of the liquid phase reagents or combined with the hydrogenation catalyst, as noted hereinbefore. In an alternative design, a liquid phase containing the nitrobenzene may be passed continuously under a hydrogen atmosphere into a hydrogenation zone containing the hydrogenation catalyst in a fixed-bed. Thereafter, the product stream from the hydrogenation zone may be co-fed with the amine into a condensation zone containing a homogeneous or heterogeneous acid cocatalyst. The para phenylenediamine is retrieved from the product stream of the condensation zone.

Any operable process conditions can be employed in the process of this invention provided that the desired para phenylenediamine product is formed. Preferred process conditions vary depending upon the particular catalyst and reagents, the concentrations of the reagents, and the like. Typically, air is excluded from the reactor to avoid losses due to oxidation of the amine.

Usually, the process temperature ranges from about 10° C. to about 170° C., and preferably, from about 70° C. to about 100° C. In a batch reactor the pressure is autogenous, and the reaction time usually does not exceed 3 hr for nearly complete conversion of the nitrobenzene. In a batch reactor the hydrogenation catalyst and the acid cocatalyst can be used in any quantities provided that the desired para phenylenediamine product is produced. Typically, the hydrogenation catalyst is employed in an amount ranging from about 0.05 to about 20 parts per 100 parts by weight nitrobenzene, preferably, from about 0.1 to about 15 parts per 100 parts by weight nitrobenzene Typically, the acid cocatalyst is employed in an amount ranging from about 0.1 to about 20 parts per 1 part by weight nitrobenzene, preferably, from about 0.5 to about 15 parts per 1 part by weight nitrobenzene.

Alternatively, in a fixed bed, continuous flow reactor, the total pressure can vary from subatmospheric to superatmospheric, but preferably, is maintained slightly above atmospheric to exclude air from the reactor. More preferably, the total pressure ranges from about 1.2 atm to about 35 atm, preferably, from about 1.5 atm to about 5.0 atm. In a continuous flow, fixed-bed reactor, the residence time of the feedstream and the relative ratio of feed to catalyst are controlled by the space velocity. For the purposes of this invention, the liquid hourly space velocity (LHSV) is defined as the grams of liquid feedstream per gram catalyst per hr, or simply $hr^{-1}$, and ranges from about 0.01 $hr^{-1}$ to about 100 $hr^{-1}$.

When nitrobenzene or substituted nitrobenzene is contacted with hydrogen and an amine in the presence of a hydrogenation catalyst, hydrogenation inhibitor, and acid cocatalyst, as described hereinbefore, a para phenylenediamine is produced. The product may be represented by the general formula:

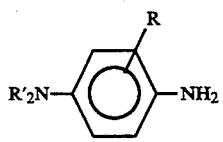

wherein R is hydrogen or representative of one or more substituents, e.g., $C_{1-10}$ alkyl moieties, mentioned in connection with the substituted nitrobenzene hereinbefore; and each R' independently may be hydrogen, alkyl, cycloalkyl, aryl or an alkaryl moiety. Preferably, each R' independently is hydrogen, a $C_{1-20}$ alkyl, $C_{4-8}$ alicyclic, or a $C_{6-15}$ aryl or alkaryl moiety. More preferably, each R' is independently hydrogen, a $C_{1-5}$ alkyl, phenyl, or $C_{1-5}$ alkyl-substituted phenyl moiety. Most preferably, R is hydrogen, one R' is hydrogen and the other R' is phenyl, and the product is p-aminodiphenylamine represented by the formula:

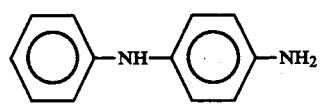

In addition to p-aminodiphenylamine, ortho aminodiphenylamine can be formed, as can azoxybenzene, azo hydrazobenzene, phenylhydroxylamine, and aniline. The quantities of these by-products depend on the particular combination of catalysts and process conditions.

Isolation of the para phenylenediamine product is accomplished using techniques well known to those skilled in the art. When the catalyst and cocatalyst are heterogeneous, the catalysts are simply filtered from the product stream. Typically, unreacted amine and any solvent are separated from the product stream by distillation. The crude para phenylenediamine may be used as is or further purified by known methods, such as fractional distillation, liquid chromatography, or recrystallization.

For the purposes of this invention, the term "conversion" refers to the weight percentage of nitrobenzene or substituted nitrobenzene which reacts to form products. The conversion varies widely depending upon the reactants, the form of the catalyst, and the process conditions, such as temperature, pressure, and flow rate. Within the preferred temperature range, as the temperature increases the conversion generally increases. Within the preferred space velocity range, as the space velocity increases the conversion generally decreases. Typically, the conversion of the nitrobenzene is greater than about 10 weight percent. Preferably, the conversion is greater than about 20 weight percent, more preferably, greater than about 40 weight percent, and most preferably, greater than about 75 weight percent.

For the purposes of this invention the term "yield" is defined as the weight percentage of converted nitrobenzene or substituted nitrobenzene which forms a specific product, such as para phenylenediamine. Yields also vary widely depending upon the reactants, the form of the catalyst, and the process conditions. Typically, the yield to para phenylenediamine is greater than about 0.5 weight percent. Preferably, the yield to para phenylenediamine is greater than about 1.0 weight percent, more preferably, greater than about 2.0 weight percent, and most preferably, greater than about 5.0 weight percent.

The following examples are presented to illustrate the process of this invention, but these examples should not be construed as limiting the scope of the invention. All percentages in the examples are weight percent unless otherwise indicated.

EXAMPLE 1

The acid form of zeolite Y is prepared as follows. The sodium ions in NaY are exchanged for ammonium ions by immersing NaY (Linde, 25 g) in a 2.0N solution of ammonium chloride (150 ml). The exchanged zeolite Y is filtered and washed three times with doubly distilled water. The exchange and washing procedures are repeated three more times. During the first three exchanges the resulting slurry is heated at reflux for 2 hr. The fourth exchange is carried out at 24° C. for 14 hr. The exchanged zeolite is dried at 110° C. for 6 hr, then calcined at 500° C. in air until no further ammonia is released. The calcination converts the ammonium-form of the zeolite into the acid form (HY) by removal of ammonia.

A Pyrex ® glass tube (3 cm×22 cm) having a frit at the bottom is filled under a helium atmosphere with 5 percent platinum on alumina (5% $Pt/Al_2O_3$, 0.2 g), zeolite Y in the acid form (1 g) prepared hereinabove, aniline (8 mL), dimethyl sulfoxide (2 mL), and nitrobenzene (1 mL). The bottom half of the tube is heated with heating tape to 160° C., and then hydrogen gas is bubbled through the tube from the bottom at a flow rate of 10 mL/min to start the reaction. At the end of a 2 hr reaction period, the liquid contents of the tube are filtered from the catalysts. The filtrate is examined by high performance liquid chromatography (HPLC) using two Waters Model 510 pumps, a Waters 490E multiwavelength detector, a U6K injector, a Baseline 810 Chromatography Workstation, and a column (4.6 mm ID×250 mm length) packed with INERTSIL TM ODS-2 (C18) brand silica. The selected wavelength is 254 nm. The mobile phase consists of an acetonitrile-water mixture flowing at a rate of 1 mL/min at ambient temperature. The volume percent of acetonitrile in the mixture is 55 percent for the first 3 min, increased to 100 percent in 5 min, held at 100 percent for 4 min, then decreased to 55 percent in 3 min. Results are set forth in Table 1.

TABLE I

| | | | | Process Conditions of Expts. 1–11 | | | | |
|---|---|---|---|---|---|---|---|---|
| Expt. | PhNO$_2$[1] (ml) | PhNH$_2$[1] (ml) | H$_2$ Cat[2] (g) | DMSO (ml) | Acid Cocat[3] (g) | T (°C.) | PH$_2$ (psig) | Time (hr) |
| 1 | 1.0 | 8 | A (0.2) | 2 | Y(1.0) | 160 | 16 | 2.0 |
| 2 | 2.0 | 20 | A (0.2) | 20 | Y(1.0) | 160 | 300 | 2.0 |
| 3 | 1.0 | 10 | A (0.1) | 10 | Y(1.0) | 160 | 300 | 0.5 |
| 4 | 2.0 | 20 | A (0.2) | 10 | F(5.0) | 100 | 100 | 1.0 |
| 5 | 2.0 | 30 | A (0.2) | 15 | F(20) | 120 | 100 | 2.5 |
| 6 | 0.2 | 2.0 | A (0.03) | 1.0 | F(2.0) | 85 | 16 | 2.2 |
| 7 | 0.1 | 4.0 | A (0.03) | 2.0 | F(2.0) | 85 | 16 | 1.3 |
| 8 | 0.05 | 1.0 | B (0.01) | 0.5 | F(1.0) | 85 | 16 | 0.5 |
| 9 | 0.05 | 1.0 | B (0.01) | 2.0 | F(1.0) | 85 | 16 | 1.0 |
| 10 | 0.05 | 2.0 | B (0.01) | 2.0 | F(1.0) | 85 | 16 | 1.2 |
| 11 | 0.05 | 2.0 | B (0.03) | 2.0 | F(1.0) | 85 | 16 | 0.3[4] |

| Expt. | Yields (mg) in Product Mixture[5] | | | Wt. % Conv. | Wt. % Yields |
|---|---|---|---|---|---|
| | PhNO$_2$ | p-ADPA | o-ADPA | PhNO$_2$ | p-ADPA |
| 1 | 1119 | 10 | 3 | 7.0 | 12.0 |
| 2 | 60 | 53 | 55 | 95.0 | 1.5 |
| 3 | 92 | 98 | 25 | 92.3 | 5.9 |
| 4 | 563 | 9 | 1 | 76.5 | 0.3 |
| 5 | 1060 | 20 | 2 | 55.8 | 1.4 |
| 6 | 135 | 4 | 0.3 | 43.8 | 2.6 |
| 7 | 0.2 | 2 | N.D.[7] | 99.8 | 1.1 |
| 8 | 0.7 | 0.4 | N.D.[7] | 98.8 | 0.5 |
| 9 | 10 | 0.9 | 0.1 | 83.3 | 1.2 |
| 10 | N.D.[7] | 1.1 | N.D.[7] | ~100 | 1.2 |
| 11 | 8.5 | 0.8 | N.D.[7] | 85.8 | 1.0 |

[1]Key: PhNO$_2$ = nitrobenzene, PhNH$_2$ = aniline, p- and o-ADPA para and ortho aminodiphenylamine
[2]A = 5% Pt/Al$_2$O$_3$, B = 5% Pt/C
[3]Y = acid zeolite HY, F = Filtrol ® grade acid clay
[4]After 2 equiv. of hydrogen are consumed, the reaction mixture is maintained at 85° C. for 20 min without stirring.
[5]Yields (mg) calculated from HPLC data using external standards to correct for response factors.
[6]Wt. % yield of P-ADPA based on converted nitrobenzene.
[7]N.D. = not detected.

EXPERIMENTS 2–5

General Procedure:

An autoclave (500 ml) is charged with nitrobenzene, aniline, a hydrogenation catalyst, a hydrogenation inhibitor consisting of dimethylsulfoxide, and an acid cocatalyst, as shown in Table I. The reactor is sealed and flushed with hydrogen gas three times. The pressure is thereafter raised to 100 psig with hydrogen gas. The temperature of the reactor is raised to that shown in the table. When the desired temperature is reached, the pressure in the autoclave is adjusted, if necessary, with additional hydrogen to that shown in the table. The reaction mixture is magnetically stirred for the duration of the reaction time. At the end of the reaction, the reactor is cooled to ambient temperature and depressurized, and the contents of the reactor are filtered to remove the solid catalysts. The filtrate for each experiment (Expt. 2–5) is analyzed by HPLC, as in Example 1, with the results set forth in Table I.

It is seen in Examples 1 through 5 that a combination of a platinum hydrogenation catalyst, dimethylsulfoxide as a hydrogenation inhibitor, and a solid acid cocatalyst can catalyze the conversion in batch of nitrobenzene, hydrogen, and aniline to p-aminodiphenylamine. In particular, zeolite Y in the acid form and Filtrol TM grade aluminosilicate clay are satisfactory solid acid catalysts for the process.

EXAMPLES 6–11

Examples 6 through 11 comprise contacting nitrobenzene with aniline and hydrogen in the presence of a hydrogenation catalyst, a hydrogenation inhibitor consisting of dimethylsulfoxide, and an acid cocatalyst. The reactions are conducted in a hydrogenation apparatus comprising a Pyrex ® cylindrical reaction chamber (15 mm×100 mm) having on its inner wall double-helical Vigreux indentations. Liquid samples are injected into the reaction chamber through a septum injection port. The reactor is pressurized with hydrogen gas from a hydrogen reservoir and heated to the desired reaction temperature. The reactor is shaken by means of an adjustable speed-drive system with a matched SCR control. Effective gas-liquid mixing is achieved at a shaking speed of between 1800 and 2000 rpm, as monitored -by a digital stroboscope. The rate of hydrogen consumption is electronically monitored by transforming the pressure changes in the hydrogen reservoir into electrical signals which are amplified and recorded. A trace of the rate is furnished on a strip chart recorder (Fisher Recordall Series 5000). Chromatographic analyses are performed as in Example 1 with the results shown in Table I.

It is seen that a platinum hydrogenation catalyst combined with dimethylsulfoxide as a hydrogenation inhibitor and an acid clay as a solid acid cocatalyst can catalyze the conversion in batch of nitrobenzene, hydrogen, and aniline to p-aminodiphenylamine.

EXAMPLES 12-15

Examples 12 through 15 are carried out in the manner described hereinabove in Examples 6-11, with the exception that a sulfide or mercaptan hydrogenation inhibitor is employed. Results are are set forth in Table II.

TABLE II[1]

Process Conditions of Expts. 12-17

| Expt. | PhNO$_2$ (ml) | PhNH$_2$ (ml) | H$_2$ Cat[2] (g) | Inhb[3] (ml) | Acid Cocat[4] (g) | Time[5] (hr) |
|---|---|---|---|---|---|---|
| 12 | 0.05 | 2.0 | B (0.01) | DMS (0.5) | F (1.0) | 1.0 |
| 13 | 0.05 | 1.0 | A (0.05) | PT (0.0005) | F (0.5) | 0.9 |
| 14 | 0.27 | 2.0 | A (0.05) | PT (0.001) | F (0.5) | 1.8 |
| 15 | 0.20 | 2.0 | A (0.05) | PT (0.001) | F (1.0) | 2.0 |
| 16 | 0.05 | 1.0 | A (0.01) | DMSO (0.3) | CF$_3$-COOH (0.3 ml) | — |
| 17 | 0.05 | 1.0 | A (0.01) | DMSO (0.3) | HCl (0.5 ml) | — |

| | Yields (mg) in Product Stream[6] | | Wt. % Conv. | Wt. % Yield.[7] |
|---|---|---|---|---|
| Expt. | PhNO$_2$ | p-ADPA | o-ADPA | PhNO$_2$ | p-ADPA |
| 12 | 46.6 | 0.6 | — | 22.3 | 5.1 |
| 13 | 37.7 | 0.4 | 0.1 | 37.3 | 1.2 |
| 14 | 155.0 | 1.2 | 0.2 | 52.2 | 0.5 |
| 15 | 97.0 | 7.6 | 3.6 | 59.6 | 3.6 |
| 16 | 11.0 | 4.5 | N.A.[8] | 81.7 | 8.6 |
| 17 | N.D.[8] | 5.2 | N.A.[8] | 100 | 9.1 |

[1]Reactor is loaded with the indicated amounts of nitrobenzene (PhNO$_2$), aniline (PhNH$_2$), hydrogenation catalyst (H$_2$ Cat), hydrogenation inhibitor (Inhb), and acid cocatalyst (Acid Cocat) and heated at 85° C. (Expts. 12, 13, 14) or 100° C. (Expt. 15, 16, 17) for the time shown. Hydrogen pressure is 1 atm (Expts. 12, 14, 15, 16, 17) or 0.5 atm (Expt. 13). Total pressure in Expt. 13 is 1 atm, the balance being helium. Products include para/ortho aminodiphenylamine (p-/o-ADPA).
[2]A = 5% Pt/Al$_2$O$_3$, B = 5% Pt/C
[3]DMS = dimethyl sulfide, PT = 1-pentanethiol, DMSO = dimethylsulfoxide
[4]F = Filtrol ® grade acid clay
[6]Yields (mg) calculated from HPLC data using external standards to correct for response factors.
[7]Wt. % yield of P-ADPA based on converted nitrobenzene.
[8]N.D.= not detected; N.A. = not available.

It is seen that nitrobenzene and aniline can be converted in the presence of hydrogen, a platinum hydrogenation catalyst, a sulfide or mercaptan hydrogenation inhibitor, and a solid acid cocatalyst into p-aminodiphenylamine. 1-Pentanethiol is the preferred inhibitor.

EXPERIMENT 16

The glass reactor of Examples 6-11 is charged with nitrobenzene (0.050 ml), aniline (1 ml), dimethylsulfoxide (0.3 ml), and a 5% Pt/Al$_2$O$_3$ catalyst (0.01 g), as indicated in Table II. The reactor is flushed with hydrogen gas three times. The temperature of the reactor is raised to about 85° C. and the pressure is adjusted with hydrogen to between 0.2 and 0.4 atm above atmospheric pressure. Trifluoroacetic acid is injected into the reactor, and the reaction is monitored until hydrogen consumption ceases. The reactor is cooled to ambient temperature, and the contents of the reactor are analyzed by HPLC. The HPLC analysis employs an ALTEX Model 110 pump, an ISCO optical unit detector UA-5 with a fixed wavelength of 254 nm, and a column (4.6 mm ID×250 mm length) packed with INERTSIL TM ODS-2 (C18) brand silica. The mobile phase consists of an acetonitrile-water mixture (50:50 volume percent), flowing at a rate of 0.5 ml/min at ambient temperature. Results are set forth in Table II. It is seen that trifluoroacetic acid functions satisfactorily as the acid cocatalyst in the process of the invention.

EXPERIMENT 17

An experiment is repeated in a manner similar to Experiment 16, with the exception that concentrated hydrochloric acid is employed instead of trifluoroacetic acid. Process conditions and results are set forth in Table II. It is seen that hydrochloric acid functions satisfactorily as the acid cocatalyst in the process of the invention.

What is claimed is:

1. A process of preparing para phenylenediamines comprising contacting nitrobenzene or a substituted nitrobenzene with hydrogen and an amine, the amounts of hydrogen and amine relative to nitrobenzene being sufficient to prepare a para phenylenediamine, the contacting being conducted in the presence of catalytic amounts of a hydrogenation catalyst, a hydrogenation inhibitor, and an acid cocatalyst, the contacting being conducted under reaction conditions such that a para phenylenediamine or a substituted derivative thereof is formed.

2. The process of claim 1 wherein nitrobenzene is employed.

3. The process of claim 1 wherein the nitrobenzene is substituted with a C$_{1-10}$ alkyl moiety.

4. The process of claim 1 wherein the amine is selected from the group consisting of ammonia, C$_{1-20}$ alkyl amines, C$_{4-8}$ alicyclic amines, and C$_{6-15}$ aryl and alkaryl amines.

5. The process of claim 4 wherein the amine is a C$_{1-5}$ alkyl-substituted aniline.

6. The process of claim 4 wherein the amine is aniline.

7. The process of claim 1 wherein the molar ratio of amine to the nitrobenzene ranges from 2 to about 25.

8. The process of claim 1 wherein the hydrogenation catalyst is selected from the group consisting of Group VIII metals, molybdenum and copper, optionally bound to a support.

9. The process of claim 1 wherein the hydrogenation inhibitor is a sulfur-containing organic compound.

10. The process of claim 9 wherein the hydrogenation inhibitor is selected from the group consisting of dimethylsulfoxide, dimethyl sulfide and 1-pentanethiol.

11. The process of claim 1 wherein the hydrogenation catalyst and hydrogenation inhibitor are combined in one compound and selected from the group consisting of noble metal sulfides and molybdenum sulfide.

12. The process of claim 1 wherein the acid cocatalyst is a homogeneous acid selected from the group consisting of hydrochloric and trifluoroacetic acids; or alternatively, is a heterogeneous solid acid selected from the group consisting of metal oxides and mixed metal oxides of the Groups IVA and VB metals, silicon oxide, and aluminum oxide; acid clays, aluminosilicate zeolites, and sulfonic acid functionalized cation exchange resins.

13. The process of claim 12 wherein the acid cocatalyst is hydrochloric acid.

14. The process of claim 12 wherein the acid cocatalyst is an acid zeolite Y.

15. The process of claim 12 wherein the acid cocatalyst is an aluminosilicate clay.

16. The process of claim 1 wherein the molar ratio of hydrogen to the nitrobenzene ranges from 2 to about 50.

17. The process of claim 1 wherein the temperature ranges from about 10° C. to about 170° C., the total pressure ranges from about 1.2 to about 35 atmospheres, and if the reactor is a flow reactor, the liquid hourly space velocity ranges from about 0.01 hr$^{-1}$ to about 100 hr$^{-1}$.

18. The process of claim 1 wherein the para phenylenediamine is represented by the formula:

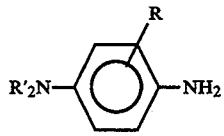

wherein R may be hydrogen or at least one substituent selected from the group consisting of $C_{1-10}$ alkyl moieties; and each R' independently may be hydrogen, $C_{1-20}$ alkyl, $C_{4-8}$ cycloalkyl, or $C_{6-15}$ aryl or alkaryl.

19. The process of claim 18 wherein R is hydrogen, one R' is hydrogen, and the other R' is phenyl, and the para phenylenediamine is p-aminodiphenylamine represented by the formula:

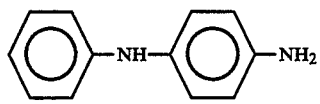

20. The process of claim 1 wherein the conversion of the nitrobenzene is greater than about 40 weight percent and wherein the yield to para phenylenediamine is greater than about 2 weight percent.

21. A process of preparing p-aminodiphenylamine comprising contacting nitrobenzene, hydrogen and aniline, wherein the molar ratio of hydrogen to nitrobenzene ranges from 2 to about 50, and wherein the molar ratio of aniline to nitrobenzene ranges from about 2 to about 25, the contacting occurring in the presence of catalytic amounts of a platinum hydrogenation catalyst supported on carbon or alumina; a hydrogenation inhibitor selected from the group consisting of dimethylsulfoxide, 1-pentanethiol, or dimethyl sulfide; and an acid cocatalyst selected from the group consisting of hydrochloric acid, trifluoroacetic acid, acid zeolite Y, and aluminosilicate clay; the contacting occurring at a temperature in the range from about 10° C. to about 170° C. and a total pressure in the range from atmospheric to about 50 arm such that p-aminodiphenylamine is formed.

22. A process of preparing para phenylenediamines comprising contacting under reaction conditions nitrobenzene or a substituted derivative thereof with hydrogen in a hydrogenation zone in the presence of a catalytic amount of a hydrogenation catalyst and in the presence of a hydrogenation inhibitor to yield a first product stream, and thereafter contacting the first product stream with an amine in a condensation zone with a catalytic amount of an acid cocatalyst under reaction conditions such that a p-phenylenediamine is formed.

* * * * *